United States Patent [19]

Melancon

[11] Patent Number: 4,922,113

[45] Date of Patent: May 1, 1990

[54] PROCESS FOR FLUORIMETRIC MONITORING OF FUNCTIONAL COATINGS AND COMPOSITIONS AND FLUORESCENT AGENTS THEREFOR

[75] Inventor: Kurt C. Melancon, St. Paul, Minn.

[73] Assignee: Minnesota Mining and Manufacturing Company, St. Paul, Minn.

[21] Appl. No.: 165,014

[22] Filed: Mar. 7, 1988

Related U.S. Application Data

[62] Division of Ser. No. 883,926, Jul. 10, 1986.

[51] Int. Cl.$^5$ ............................................. G01N 21/64
[52] U.S. Cl. .................................. 250/372; 250/458.1; 250/461.1
[58] Field of Search ................... 250/372, 461.1, 458.1, 250/459.1

[56] References Cited

U.S. PATENT DOCUMENTS

| | | | |
|---|---|---|---|
| 3,019,336 | 1/1962 | Johns | 250/308 |
| 3,118,060 | 1/1964 | Klein | 250/302 |
| 3,130,303 | 4/1964 | Dobbins | 250/388 |
| 3,341,010 | 9/1967 | Switzer | 209/111.5 |
| 3,547,827 | 12/1970 | Switzer | 252/301.2 |
| 3,577,885 | 5/1971 | Wells | 250/459.1 |
| 3,675,015 | 7/1972 | Geib | 250/302 |
| 3,871,885 | 3/1975 | Hertler | 96/35.1 |
| 3,912,928 | 10/1975 | Rush et al. | 250/459.1 |
| 3,930,063 | 12/1975 | Miller et al. | 427/54 |
| 3,956,630 | 5/1976 | Mellows | 250/302 |
| 3,965,350 | 6/1976 | Molina | 250/461.1 |
| 4,058,732 | 11/1977 | Wieder | 250/461.1 |
| 4,109,152 | 8/1978 | Aoki et al. | 250/486.1 |
| 4,152,723 | 5/1979 | McMahon et al. | 250/458.1 |
| 4,250,382 | 2/1981 | Libby | 250/302 |
| 4,536,654 | 8/1985 | Vaerman | 250/461.1 |
| 4,621,193 | 11/1986 | Van Hoye | 250/461.1 |
| 4,684,678 | 8/1987 | Schultz et al. | 523/466 |
| 4,755,684 | 7/1988 | Leiner et al. | 250/461.1 |

FOREIGN PATENT DOCUMENTS

| | | |
|---|---|---|
| 1422526 | 1/1976 | United Kingdom . |
| 2016370 | 9/1979 | United Kingdom . |
| 2194244 | 3/1988 | United Kingdom . |

OTHER PUBLICATIONS

De Silva, J. A. F. et al., "Luminescence Determination of Pharmaceuticals of the Tetrahydrocarbazole, Carbazole and 1,4-benzodiazepine Class", *Analytical Chemistry*, vol. 48, No. 1, pp. 144–155, Jan. 1976.

*Radio Shack Dictionary of Electronics*, compiled by Rudolph Graf, pub. by Tandy Corp., pp. 632 & 646, entries for "ultraviolet" and visible radiation, 1974.

Farrand Optical Co., Inc., Listing of Activation and Fluorescent Peaks of Various Compounds, May, 1950's.

Thommes et al., "The Spectrofluorometric Determination of Anthracene, Fluorene, and Phenanthrene in Mixtures", *Talanta*, vol. 7, pp. 181–186, (1961).

White et al., *Fluorescence Analysis–A Practical Approach*, Marcel Dekker, Inc., 1970, New York, pp. 200–209.

G. W. Jones et al., IBM Technical Disclosure Bulletin, vol. 27, No. 4A, Sep. 1984, p. 2202.

*Primary Examiner*—Constantine Hannaher
*Attorney, Agent, or Firm*—Donald M. Sell; Walter N. Kirn; Lorraine R. Sherman

[57] ABSTRACT

A method for monitoring the coating weight, uniformity, defects or markings present in a coating of a composition applied to a substrate comprises the steps:

(a) providing a substrate with a functional coating of a composition comprising an effective amount of uvescer that absorbs radiant energy, i.e., has an excitation energy, of wavelength $\xi_1$ and emits radiant energy of wavelength $\lambda_2$;

(b) scanning the coating with radiant energy having a wavelength within wavelength $\lambda_1$;

(c) detecting the radiant energy of wavelength $\lambda_2$ emitted by the coating; and (d) optionally, correlating the emitted radiant energy to independently measured standard coating weights or thicknesses, of the coating so as to measure coating weight, thickness, uniformity, defects, or markings.

31 Claims, No Drawings

PROCESS FOR FLUORIMETRIC MONITORING OF FUNCTIONAL COATINGS AND COMPOSITIONS AND FLUORESCENT AGENTS THEREFOR

FIELD OF THE INVENTION

This is a division of application Ser. No. 883,926 filed July 10, 1986.

The present invention relates to a method of detecting thickness, uniformity, and defects in coatings and detecting marking in coatings that have been applied to substrates, utilizing uvescence, i.e., fluorescence in the ultraviolet region of the electromagnetic spectrum. In another aspect it relates to uvescing compounds suitable for such use and compositions containing them.

BACKGROUND ART

Very few articles of commerce and general use do not have a coating of some kind for the enhancement of appearance, scratch and abrasion resistance, moisture proofing, adhesion or release of other materials, or alteration of some other characteristics of the surface of the article. Since the quality and cost of the coating is dependent on the coating weight and uniformity it is desirable that a means for monitoring these characteristics be employed.

The use of radiation to measure thickness of coatings has been taught. U.S. Pat. Nos. 3,019,336 and 3,130,303 disclose that beta rays emanating from a radioactive source such as strontium-90 and directed toward a coating are backscattered in an amount related to the thickness of the coating. Such a technique cannot be used to monitor coating uniformity and coating defects during manufacture of web materials bearing thin coatings. In this technique only the average coating weight can be determined, not the weight at any specific point.

U.S. Pat. Nos. 3,675,015, 3,118,060, 3,930,063, 3,956,630 and 4,250,382 disclose methods and apparatus for continuously monitoring coating weight of a coating on a web or fiber. For these methods, a fluorescing compound, dye or pigment, is added to the coating formulation and the fluorescence of the coating in the visible range of the electromagnetic spectrum is continuously and quantitatively measured while the coating is exposed to ultraviolet radiation. Fluorescence readings taken in the cross direction and machine direction of the web give an indication of the lay of the coating on the web. These techniques, although useful for monitoring coatings on some webs, e.g. paper or fiber, are not satisfactory for monitoring coatings on webs which also fluoresce, such as paper treated with an optical brightener to enhance whiteness. Further, it is stated in U.S. Pat. No. 4,250,382 (col. 2, lines 10-12) that fluorescent dyes have not been found satisfactory for detecting coatings of cured polysiloxane resins.

SUMMARY OF THE INVENTION

The present invention, which provides a method for monitoring a functional coating composition applied to a substrate, comprises the steps:

(a) providing a substrate with a functional coating of a composition comprising an effective amount of a uvescer that is an organic or inorganic compound that absorbs radiant energy, i.e., has an excitation energy, of wavelength $\lambda_1$ and emits radiant energy of wavelength $\lambda_2$; $\lambda_1$ and $\lambda_2$ each being wavelengths within the ultraviolet portion of the electromagnetic spectrum;

(b) scanning the coating with radiant energy having a wavelength within the range of wavelength $\lambda_1$; and (c) detecting the radiant energy of wavelength $\lambda_2$ emitted by the coating; and (d) optionally, correlating the emitted radiant energy to independently measured weights or thicknesses of the coating.

The functional coating composition of the invention can be monitored for defects, average weight, uniformity, markings as for registry, alignment, images, or coded information by the method of the invention.

Prior art coatings which depend on luminescent components for monitoring provide extraneous light when the article is viewed. This light will change appearances and color fidelity in an article. In contrast, coatings of the present invention which utilize uvescers (which do not emit visible light) cannot change the appearance or color fidelity of an article.

The instant invention is particularly useful when the substrate to which a coating is being applied is one that fluoresces (contains a luminescer), i.e., absorbs radiant energy of a wavelength in the ultraviolet and emits most or all of its radiation in the visible and/or near ultraviolet portion of the electromagnetic spectrum. The substrate fluorescence in the instant invention does not mask the ultraviolet emission of the coating.

Prior art coatings applied to substrates that fluoresce cannot be accurately monitored in the visible range because of interference by the substrate fluorescence which masks the visible emission of the coating. In contrast, coatings of the present invention function satisfactorily on substrates that fluoresce in the visible range because emission is monitored in the ultraviolet range.

In another aspect of the invention, there are provided functional coating compositions that can be monitored for thickness, uniformity, and defects. The invention also provides substrates bearing a layer of such compositions including discontinuous coatings such as marks, images, or coded information.

Uvescers useful in the invention generally absorb radiant energy of wavelength $\lambda_1$, which is in the ultraviolet range. The wavelength should generally be below 400 nm and should generally be above 240 nm because this minimizes interference from any visible radiation emitted by the substrate; the uvescer emits in a wavelength $\lambda_2$, which generally is less than 430 nm with no more than 30 percent of the emitted light having a wavelength greater than 400 nm and preferably is less than 350 nm. This allows for minimization of interference from any visible radiation that may be emitted by the substrate.

The process of the invention is particularly desirable for those coatings having a utility that requires expensive components and/or for which coating thickness and uniformity are critical, especially where loss as a result of flaws and of non-optimal coating weight cannot be tolerated. Generally, such coatings can be from about 0.01 to about 200 or more micrometers in thickness, and for release coatings 0.01 to 10 micrometers may be preferred. Examples of such functional coating compositions include primer coatings for enhancing the adhesion of subsequently applied top coatings; protective coatings such as moisture resistant and abrasion-resistant coatings; radiation-sensitive imageable layers; adhesive coatings such as those based on synthetic and natural rubber, acrylic, epoxy, and silicone compounds; and release or abherent coatings such as those based on polymers of long chain aliphatic compounds, silicone resins and fluorochemicals.

Prior art coatings which depend on luminescent components for monitoring, emit visible light when the article is viewed. As noted above, this light will change color fidelity of the article.

In contrast, the present invention provides for monitoring by means of uvescers which emit most of their energy in the ultraviolet range. The amount of visible light emitted is small and hence cannot modify or alter the color of the article.

In this application:

"fluorescence" means emission of a photon from a substance, occurring as a result of a spin conserving transition from an excited electronic state to a lower energy electronic state;

"phosphorescence" means the emission of a photon from a molecule, occurring as a result of a non-spin conserving transition from an excited electronic state to a lower energy electronic state;

"uvescence" means fluorescent or phosphorescent emission in the ultraviolet portion of the spectrum;

"luminescence" means fluorescent or phosphorescent emission in the visible portion of the spectrum;

"uvescer" means a uvescent compound or substance which bears a uvaphore group or radical which on illumination by radiation in the ultraviolet portion of the spectrum emits ultraviolet radiation and differs from luminescent compounds of the prior art which emit light in the visible portion of the spectrum above about 400 nm;

"functional coating composition" is a term applied to any coating composition having utility;

"organic" means any compound including an organic group, e.g., an organometallic compound; and "uvaphore" means a group or radical which may be mono- or polyvalent, which confers uvescence upon a monomeric compound or polymer comprising it.

DETAILED DESCRIPTION OF THE INVENTION

The functional coating composition comprises (1) a monomeric or polymeric composition that can be thermoplastic and/or curable that provides the characteristics necessary to produce the function of the coating and adjuvants for modifying these characteristics, (2) an effective amount of a uvescer that (a) absorbs radiant energy of wavelength $\lambda_1$, (b) emits radiant energy of wavelength $\lambda_2$, $\lambda_1$ and $\lambda_2$ each being wavelengths or ranges of wavelengths within the ultraviolet portion of the electromagnetic spectrum, and the mean of the range of $\lambda_2$ is above the mean of the range of $\lambda_1$ in the electromagnetic spectrum.

In one embodiment, $\lambda_1$ represents one or more wavelengths in the range of 240 to 400 nm, and $\lambda_2$ represents a range of wavelengths of the emitted radiant energy below about 430 nm, not more than 30% of which has a wavelength above 400 nm, and preferably is in the range of 280 to 400 nm, and most preferably 290 to 350 nm. In the case of a uvescer, the coating composition has a product ($\epsilon\phi$) of molar extinction (molar absorptivity) coefficient ($\epsilon$) and quantum yield ($\phi$) of at least 1000. Preferably, the product ($\epsilon\phi$) is 10,000 or more. ($\epsilon$) and ($\phi$) are defined in A. J. Gordon et al. "The Chemist's Companion", Wiley-Interscience Publication, John Wiley & Sons, New York (1972), particularly pages 211 and 362.

The product of the molar extinction coefficient and the quantum yield is a measure of the efficiency of a uvaphore, the greater the product the higher the efficiency of the uvaphore. The preferred ranges allow for minimal interference from any visible radiation emitted by the substrate.

Uvescers which absorb radiation in the range of 240 to 290 nm and emit radiation in the range of 290 to 350 nm do not absorb solar ultraviolet radiation which is in the range of 295 to 400 nm. These uvescers thus have the advantage in contrast to prior art luminescers, that they cannot act as sensitizers for the solar photodegradation of a coating or substrate.

Substrates to which the coating composition of the invention can be applied include any solid surface, for example, those of paper, cardboard, wood, cork, plastic such as polyester, polyurethane, polyamide, polycarbonate, polyolefin, etc., woven and nonwoven fabric such as cotton, polyester, polyolefin, nylon, etc., metals such as aluminum, iron, etc. glass, fused silica, ceramic, etc., including fabrics made therefrom. Substrates which are continuous webs or fibers are particularly applicable to the process of the invention and may be inspected "on-line" to permit continuous control of the process variables.

Substrates that fluoresce or phosphoresce above about 350 nm, particularly those that fluoresce or phosphoresce in the visible range (about 400 to 700 nm), contain in their structure components that luminesce. These components are commonly aromatic in character, i.e., the component is a group that is more or less similar in character to benzene and can be hydrocarbyl or heterocyclic. Examples of aromatic groups that, when properly substituted, may be luminescent are phenyl, naphthyl, quinolyl, pyridyl, furyl, etc., and their corresponding polyvalent groups. Other components of substrates that can fluoresce or phosphoresce in the visible portion of the optical spectrum are luminescent inorganic pigments such as $Y_2O_3$:Eu, $YVO_4$:Eu, $La_2O_2S$:Eu, and $Zn_3Cd_2S$:Ag, and powders of minerals such as willemite, among many others.

Uvescers used in the coating composition and process of the invention should be capable of being stably dispersed (i.e., dissolved or finely divided such that on dispersing in a functional composition a suspension is formed from which less than ten percent by weight of the particles settle out in 24 hours) into a functional composition; preferably, the uvescers are soluble in the coating; and most preferably, the uvescers are reacted into the coating and become chemically bound as uvaphores therein. The material preferably is organic, i.e., it can be aromatic, aliphatic, heterocyclic, cycloaliphatic, or inorganic. As used herein, organic includes organometallic. In addition to carbon and hydrogen, the uvescer can contain one or more elements of groups 2–17 (formerly often called IIA-VIIB) of the Periodic Table of Elements as described in Chem. and Eng. News 63 (No. 5) Feb. 4, 1985 as for example oxygen, nitrogen, sulfur, chlorine, titanium, boron, vanadium, chromium, manganese, cobalt, copper, zinc, and silicon. The uvescer can be monomeric or a polymeric compound having a molecular weight of up to 500,000 or more, including crosslinked polymers

| Examples of Monomeric Uvescers include: | εφ |
|---|---|
| biphenyl | 2,900 |
| 4-methylbiphenyl | 8,000 |
| 4-benzylbiphenyl | 4,800 |
| 4-vinylbiphenyl | 18,300 |
| 4-phenoxybiphenyl | 2,200 |
| 1,3,5-triphenylbenzene | 16,200 |
| indole | 2,200 |
| azulene | 1,150 |
| naphthalene | 1,400 |
| 2-chloronaphthalene | 2,500 |
| 2-naphthol | 1,100 |
| acenaphthene | 4,400 |
| fluorene | 19,200 |
| dibenzofuran | 8,500 |
| carbazole | 1,700 |
| N-butylcarbazole | |
| N-ethylcarbazole | |
| m-terphenyl | 13,100 |
| p-terphenyl | 31,600 |
| 4-methyl-p-terphenyl | 32,000 |
| p-quaterphenyl | 35,600 |
| 2,5-diphenylfuran | 38,000 |
| 2,5-diphenyl-1,3,4-oxadiazole | 24,900 |
| 2-phenyl-5-diphenyl-1,3,4-oxadiazole | 39,800 |
| 2-phenyl-5-(2-naphthyl)-1,2,3-oxadiazole | 9,700 |
| triphenylene | 1,700 |
| dibenzothiophene | 300 |
| dibenzothiophene-9,9-dioxide | |
| 9,10-dihydrophenanthrene | |

Also intended are derivatives of these uvescers functional groups such as vinyl, vinyloxy, allyl, hydroxy, amino, carboxy, epoxy, isocyanato, acryloxy, methacryloxy, acrylamido, and hydrosilyl groups.

Compositions of the invention that are preferred comprise (1) a functional coating composition comprising a polymeric compound or polymer precursor and (2) an effective amount of a uvescent substance or more preferably of a uvaphore having attached to it one or more groups that increase the dispersibility of the uvescer in the functional coating composition, the substituted uvescer having the general formula

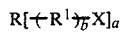

I wherein

R is a group comprising at least one uvaphore and having a valence "a", the uvaphore being a polycyclic aromatic group and having two to four aromatic rings of which at least two are joined by a single bond (e.g., as are present in biphenyl, bipyridyl, 2,5-diphenylfuran, etc.) or by fusion (e.g., naphthalene, fluorene, carbazole, dibenzofuran, etc.), the polycyclic aromatic compound absorbing radiant energy of wavelengths between 240 and 400 nm, emitting radiant energy below about 430 nm, no more than 30% of the emitted energy being above 400 nm, and having an εφ product of at least 1000, preferably in excess of 10,000; R can comprise 1 to 5 uvaphores, preferably no more than 2;

each X is independently hydrogen or B, and preferably one B group is present, in which B is a reactive group that can react to form a covalent bond with a complementary reactive group present in the polymer or polymer precursors; examples of B include a vinyl group —CH=CH₂, a vinyloxy group —OCH=CH₂, a carboxyvinyl group

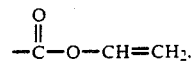

an allyl group —CH₂CH=CH₂, a hydroxy group —OH, an amino group —NH₂, a carboxy group —COOH, an epoxy group

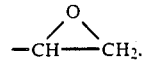

a glycidyloxy group

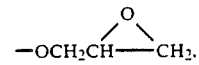

an isocyanato group —NCO, an acryloxy group

a methacryloxy group

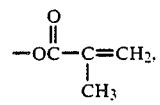

an acrylamido group

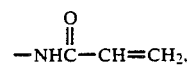

or a hydrosilyl group —Si(R³)₂H in which R³ is independently a methyl, ethyl, or phenyl group, R¹ is an alkylene or alkenylene group, preferably being omega unsaturated, the group having 1 to 18 carbon atoms;

a is an integer having a value from one to three, inclusively; and b is zero or one, b being one when X is hydrogen.

Examples of preferred uvescers for functional coating compositions include the following compounds and their derivatives:

4-butylbiphenyl
N-pentylindole
1-heptylnaphthalene
1-vinylnaphthalene
2-(5-hexenyl)naphthalene
1-naphthalenecarboxylic acid
1-naphthaleneneisocyanate
2-(5-isocyanatopentyl)naphthalene
1-(7-octenyl)naphthalene
1-trimethylsilylacenaphthylene
1-aminonaphthalene
1-acrylamidonaphthalene
2-acryloyloxynaphthalene
2-methacryloyloxynaphthalene
9-[(2-acryloyloxy)ethylcarbamoyl]-9H-fluorene
biphenyl
triphenylbenzene
fluorene
carbazole
terphenyl quaterphenyl
triphenylene
naphthalene
2,5-diphenylfuran
dibenzofuran
2,5-diphenyl-1,2,4-oxadiazole
2,3-epoxypropoxynaphthalene
4-heptyl-p-terphenyl
4-(undec-10-enoyl)-p-terphenyl
9-butylcarbazole
9-heptylcarbazole
9-allylcarbazole
9-(7-octenyl)carbazole
3-decylcarbazole
4-butyl-p-quaterphenyl
2-phenyl-5-(4-butylphenyl)furan
2,5-bis(4-butylphenyl)oxadiazole
2-hexyltriphenylene
9-isocyanatofluorene
dimethyl-1-naphthylsilane
9-allyfluorene
9-butylfluorene
4-butylfluorene
9-(7-octenyl)fluorene Uvescers that are particularly preferred for use in the compositions of the invention are polymeric uvescers that are organic condensation or addition polymers having one or more terminal or pendent uvaphore groups attached to a polymeric backbone, the pendent uvaphore group having the formula $$R(\!(R^2)_b Y\!)_a \qquad II$$

wherein

R is the same as defined above in Formula I, $R^2$ is an alkylene or alkenylene group having 1 to 18 carbon atoms, Y is a carbon-to-carbon single bond or a divalent connecting group resulting from the reaction of a reactive group attached to the uvaphore with a complementary reactive group present in the condensation or addition polymer; representative Y groups include an oxycarbonyl group, $$-O\overset{O}{\underset{\|}{C}}-,$$

as is formed by reaction of a hydroxy groupcontaining polymer and a carboxy group attached to the uvaphore; a carbonyloxy group $$-\overset{O}{\underset{\|}{C}}O-.$$

that is formed by the reaction of a carboxy groupcontaining polymer and a hydroxy group attached to the uvaphore; a urethane group, $$-O\overset{O}{\underset{\|}{C}}NH-.$$

that is formed by the reaction of a hydroxy group-bearing polymer and an isocyanato group-bearing uvaphore; a 3-oxy-2-hydroxypropoxy group, -OCH$_2$CH(OH)CH$_2$O-, that is formed by the reaction of a hydroxy group-bearing polymer and a 2,3-epoxypropoxy group-bearing uvaphore, a silylethyl group such as -CH$_2$CH$_2$-Si(CH$_3$)$_2$- that is formed by the reaction of a vinyl substituted polymer and a dimethyl-hydrosilyl group-bearing uvaphor, and a is an interger of 1 to 3 inclusively, and b is zero or one.

Polymeric uvescers can be prepared by the reaction of a condensation or addition polymer that is to be used as the polymer or polymer precursor for a functional coating with a uvescer bearing a reactive group complementary to the reactive group of the polymer or precursor. Examples of such polymeric uvescers include polyvinylcarbamates, polyacrylates, polysiloxanes, polyethers, perfluoropolyethers, and polyesters. Specific examples of such polymeric uvescers include:

1. Polyvinylcarbamates.

The reaction product of a partially hydrolyzed polyvinylacylate, 9-isocyanatofluorene and octadecylisocyanate, the average polymer having the formula, wherein the units can be randomly arranged,

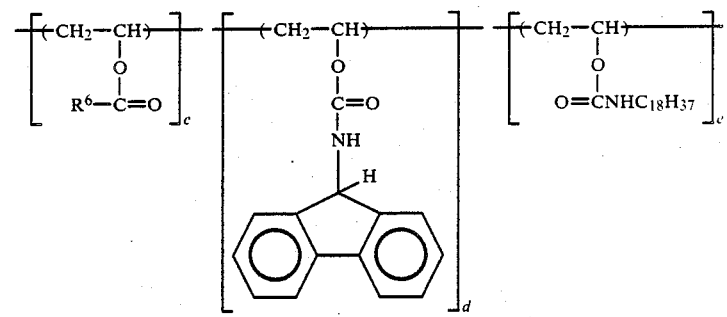

in which $R^6$ is one or more of lower alkyl groups (C$_1$ to C$_4$) or a phenyl group, and c, d, and e are integers the sum of which is about 10 to 20,000, d is 0.01% to 10% of the sum and e is 5% to 95% of the sum. Coatings of such polymers on substrates, e.g., kraft paper, polyester, polyolefin, cellulose acetate, polyolefin coated papers, and the like can function as a low adhesion backsize that can be monitored for thickness and coating defects by the process of the invention.

2. Polyacrylates.

The reaction product of a polymer of one or more acrylic esters of non-tertiary alkanols having 4 to 12 carbon atoms and one or more of acrylic acid, methacrylic acid, or itaconic acid with 2-(5-isocyanatopentyl)naphthalene, the polymer having randomly arranged units in an average formula of the structure:

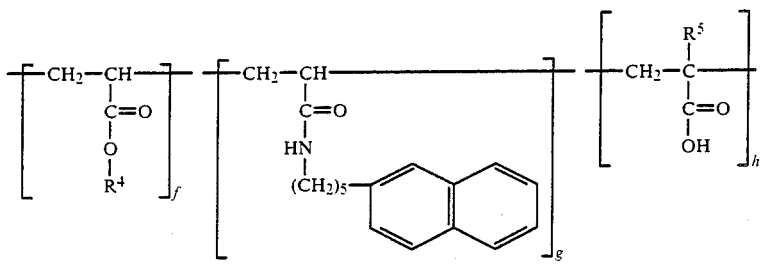

in which $R^4$ is a primary or secondary alkyl group having 4 to 12 carbon atoms and $R^5$ is hydrogen, methyl, or carboxymethyl and f, g, and h are numbers the sum of which is about 10 to 20,000, g is 0.01 to 10% of the sum and h is 0 to 75% of the sum. Coatings of such polymers are functional as pressure-sensitive adhesives that can be monitored for thickness and coating defects by the process of the invention.

3. Polysiloxanes.

The hydrosilation reaction product of hydride-functional polydimethylsiloxane fluids with 9-allyl fluorene having the average formula, wherein the units can be randomly arranged,

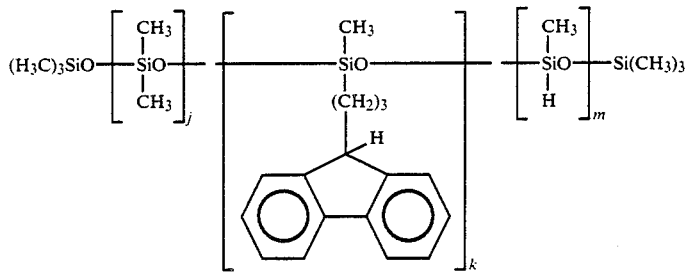

or

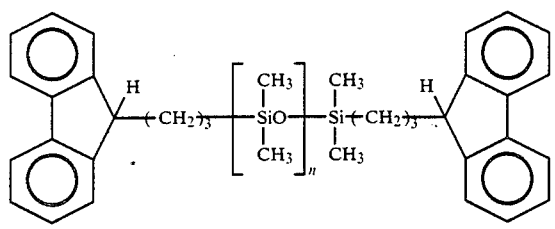

in which j, k, and m are numbers the sum of which is about to 10,000, k being from about 0.01 to 10% of the sum of j, k and m, m being from zero to about 99.5% of the sum of j, k and m, and n being a number from about 5 to 10,000. Such polymers, if contained in coatings on a substrate, are functional as release surfaces, or they can be dispersed in polysiloxanes to form compositions that can be coated and monitored for thickness, uniformity, and defects by the process of the invention.

4. Perfluoropolyethers.

The reaction product of 9-aminofluorene with a dimethylester terminated perfluoropolyether, the average polymer having the formula:

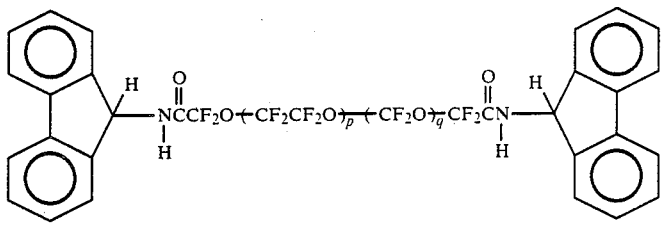

in which integers p and q designate the number of randomly distributed perfluoroethyleneoxy and perfluoromethyleneoxy backbone repeating subunits respectively, the ratio p/q being 0.2/1 to 5/1, said compounds having a number average molecular weight in the range of 500 to 20,000 or higher, preferably 800 to 15,000.

5. Polyethers.

The reaction product of a functional group substituted uvescer such as, for example, 9-isocyanatofluorene and polyoxyalkylenepolyols, such as the reaction product of 9-isocyanatofluorene with the ethyleneoxide adduct of a polyol having an average formula of the structure

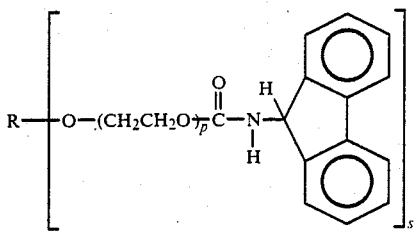

in which p designates the number of ethyleneoxy units and is a number from 1 to 30 or more, R is hydrogen or an alkyl, cycloalkyl, heterocyclic, or aryl group having a valence of s and s is an integer of 1 to 6 and, preferably, the reaction product has a molecular weight of 15 to 1000.

6. Polyesters.

The reaction product of one or more dicarboxylic acids and one or more polyols having from 2 to 6 hydroxyl groups in which at least one of the dicarboxylic acids and/or polyols is substituted by a uvaphore group to provide in the polyester uvescer a concentration of about 1 to 50% by weight uvaphore. An example of such a polyester uvescer is the reaction product of diethyleneglycol and 2,5-bis(4-carboxyphenyl)furan and adipic acid. The reaction product has the average formula of the structure:

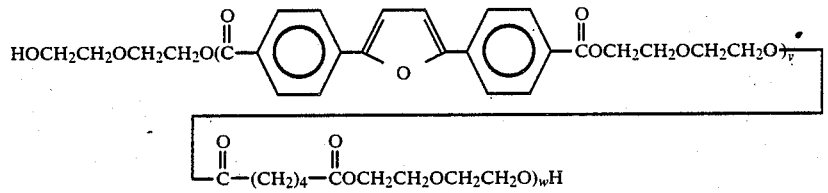

in which v designates the number of uvaphore ester units in the reaction product and is a number from 1 to about 20 and w designates the number of ethyleneoxyethylene adipate units in the reaction product and is zero or a number up to about 30 and the molecular weight of the reaction product is from about 300 to 10,000.

Monomeric uvescers can be present in an amount in the range of 0.001 to 10 weight percent, preferably 0.01 to 5 weight percent of the coating composition. Polymeric uvescers can be present in amounts up to 100% of the coating composition. Generally, the amount of polymeric uvescers used is such that the uvaphore component of the polymeric uvescers is present at a concentration of 0.001 to 10 weight percent of the total coating composition.

A maximum effective amount of a uvescer for measuring thickness is an amount sufficient to allow ultraviolet radiation to penetrate the coating to its full depth and provide a maximal emitted signal consistent with there being a measurable signal from the entire depth of the coating. Amounts in excess of an effective amount will tend to absorb all of the ultraviolet radiation in the upper portion of the coating and will provide no useful signal from the lower portion to indicate its thickness. Amounts less than the maximum effective amount may be highly satisfactory or even preferred if it is desired that the coating weight be directly proportional to the measured signal. The maximum effective amount allows for measuring coating thickness as well as for detecting coating voids. For detecting coating voids amounts of uvescer may be substantially greater than the maximum effective amount useful for measuring thickness.

To determine the maximum effective amount of uvescer for a particular application it is necessary to establish the range of coating thickness for which a measurement is desired. At the maximal thickness, ultraviolet radiation must penetrate to the base of the coating to a sufficient degree to provide a useful signal. This can be established by coating the uvescer-containing composition on a substrate transparent to ultraviolet radiation and measuring the ultraviolet radiation transmission of $\lambda 1$. The coating should have an absorbance no greater than 1.0 (the absorbance varies with thickness and amount of uvescer). For each application the maximum effective amount of uvescer should be individually determined.

The compositions of the invention that can be monitored for thickness, uniformity, and defects and inspected for markings by the process of the invention are prepared from any of the coating compositions known in the coating art that are not opaque to radiant energy of $\lambda_1$ or $\lambda_2$ (e.g., paints containing pigments such as titanium oxide and adhesive compositions containing phenolic resins which would absorb more than about 90% of the radiant energy of $\lambda_1$ could not be monitored but any coating transparent to more than about 10% of the radiant energy of $\lambda_1$ could be monitored; these limits do not apply if only voids are to be detected). There is added to the coating composition 0.001 to 10 weight percent of the uvescer and the mixture is stirred or homogenized until the uvescer is uniformly dispersed or preferably is dissolved. In some cases, the uvescer reacts with the coating and becomes incorporated therein as a uvaphore. These are preferred embodiments of the present invention. The composition is then coated onto a substrate by any technique known in the art including spraying, curtain coating, direct or reverse roll coating, dipping, brushing, extruding, and printing. The coating may be continuous or discontinuous and can include images or markings intended as process signals or as coded product information. Solvent, when used, is then removed from the coating by air drying, heating, vacuum drying, etc. as is known in the art. Then, after or preferably before curing by heat or exposure to actinic radiation (e.g., ultraviolet, infrared, x-ray, etc.) or electron-beam, when desired, the coated substrate is illuminated with radiant energy of a wavelength that can excite the uvescer into uvescence (energy in the ultraviolet within the range of $\lambda_1$) and the emitted energy of uvescence in the ultraviolet portion of the spectrum, $\lambda_2$, measured. An instrument suitable for use in illuminating the coated substrate with excitation energy and measuring the energy of uvescence is a fluorescence spectrophotometer such as the model No. MPF-44B Fluorescence Spectrophotometer supplied by Perkin-Elmer, Norwalk, Conn. Illumination of the coated substrate can also be provided by other sources of illumination known in the art such as by use of xenon arcs, mercury arcs, ultraviolet lasers, and "black lamps". The use of filters to isolate a particular wavelength is often desirable. The uvescent emission from the coatings can be measured by means of photodiodes or phototubes.

The emitted energy of uvescence is then correlated to coating weight or thickness of the coating as determined by an independent method such as gravimetric analysis, ash determination, ellipsometry, chemical, or radiochemical analysis, etc. A plot of emission energy versus coating weight is then made. Readings on the graph provide a standard which represents a correlation between uvescent emission and coating weight for a particular coating. When the emission energy of the coating deviates from that for the desired coating thickness, the coating process is adjusted to obtain the uvescent energy indicative of the desired coating thickness.

Voids, variations in coating uniformity, and other defects occurring in the coating are also made apparent by changes in the emission energy of the coating. Steps can then be taken to correct such undesirable occurrences.

Substrates bearing functional layers or articles comprising functional layers such as primer compositions, protective coatings such as moisture resistant or abrasion resistant coatings, adhesive coatings, lubricating coatings, radiation-sensitive imageable coatings, and release or abherent coatings can advantageously be coated with compositions of the invention. Such uvescercontaining layers can be monitored, using the method of the present invention, for coating thickness, uniformity, and defects. Furthermore, any subsequent overcoatings may be monitored if they absorb some or all of either $\lambda_1$ or $\lambda_2$, since the presence of voids will be readily detected, while thickness may be adjudged by the degree of attenuation of the signal. This same principle can be used to provide markings or images for the aforementioned purposes.

In addition, the presence of a first article which is to be adhered to a second article can be ascertained if the first article comprises a functional coating of the instant invention. For example, the presence of a release liner on an article can be detected if the release liner comprises a uvescer as taught in the present invention.

Objects and advantages of this invention are further illustrated by the following examples, but the particular materials and amounts thereof recited in these examples, as well as other conditions and details, should not be construed to unduly limit the invention.

EXAMPLE 1

This example describes a solventless silicone release coating composition containing a soluble, essentially non-volatile, reactive uvescer; coating and curing the release composition on a substrate to yield release liners of varied coating weight; and analyzing the release liners on a fluorescence spectrophotometer to show the correlation between coating weight and uvescent emission level.

To a solution consisting of 99 g of a dimethylvinyl-chainstopped polydimethylsiloxane fluid with a viscosity of 350 cps and 1.0 g 9-allylfluorene was added a platinum/vinyl siloxane catalyst (see U.S. Pat. No. 3,715,334, EXAMPLE 5) to provide 100 parts of platinum metal per 1,000,000 parts of silicone composition. After mixing for 10 min., 0.25 g 2-ethylhexylhydrogen maleate hydrosilation inhibitor was added and the catalyzed inhibited silicone solution was mixed for an additional 10 min. Next, there was added 2.5 g of a trimethyl-chainstopped polymethylhydrogen siloxane fluid having a viscosity of 70 cps. The resultant mixture was stirred for 15 min. more to yield a solventless, thermally curable silicone release coating composition containing a soluble, virtually non-volatile, reactive uvescer.

The silicone coating composition was then applied to 60 lb. brown super-calendered kraft paper (weighing about 105 g/m$^2$) at 4 coating weights with a 3-roll differential speed offset gravure coater, equipped with a 79 line/cm (200 line/inch) gravure cylinder, a rubber transfer roll, and a steel back-up roll; the transfer and back-up rolls turned at a surface speed of 13.7 m/min (45 ft/min.), and the gravure roll turned first at 4.1 m/min (13.5 ft/min.), then at 3.03 m/min (10.0 ft/min.), then at 2.69 m/min. (9.0 ft/min.), and finally at 2.02 m/min (6.75 ft/min.) to provide 4 samples of different coating weights. These coated samples were cured in a forced air oven at 300° C. for 60 sec. to provide 4 samples of release liners containing a chemically bound uvaphor. The resultant coating weights were determined by analysis on a Princeton Gamma-Tech ™ model No. 100 Fluorescent Chemical Analyzer, Princeton Gamma-Tech, Inc., Princeton, N.J. and the average of 5 values showed the coating weights to be 1.22 g/m$^2$, 1.03 g/m$^2$, 0.96 g/m$^2$, and 0.77 g/m$^2$, respectively, as standard for correlation to uvescent data of the invention. (Differential-speed coating of silicones is described in U.S. Pat. No. 4,216,252).

The 4 samples of release liner thus prepared were analyzed on a Perkin-Elmer MPF-44B Fluorescence Spectrophotometer, Perkin-Elmer, Norwalk, Conn. utilizing an excitation wavelength of 260 nm while measuring the uvescent emission level at a wavelength of 315 nm. The uvescent emission level was measured 5 times for each sample and the average emission level for each coating weight is reported in Table I.

TABLE I

| Sample | Coating weight (g/m$^2$) | Uvescent emission level |
|---|---|---|
| 1 | 1.22 | 85 |
| 2 | 1.03 | 63 |
| 3 | 0.96 | 46 |
| 4 | 0.77 | 40 |

The data of Table I show the strong correlation between coating weight and uvescent emission level: i.e., as coating weight decreases the uvescent emission level also decreases.

EXAMPLE 2

This example describes the preparation of an organic based thermoplastic release composition that contains a chemically bound uvaphore; coating the release composition on a substrate to yield release liners of varied coating weight; and analyzing the release liners on a fluorescence spectrophotometer to show the correlation between coating deposition and uvescent emission level.

To a 1-liter 3-necked round-bottom flask equipped with a Dean-Stark water trap, reflux condenser, static nitrogen atmosphere, and mechanical stirrer was added 218 g xylene and 30 g of partially hydrolyzed polyvinyl acetate with a degree of hydrolysis of about 50%. The polyvinyl acetate dispersion was azeotroped to dryness at atmospheric pressure before a solution containing 62.2 g octadecylisocyanate, (Mondur O ™, Mobay Chem. Co., Pittsburgh, Pa.) and 0.94 g 9-isocyanatofluorene was added to the flask and the reaction maintained at reflux for 20 h. An aliquot removed from the flask and analyzed by infrared spectroscopy showed only a trace of isocyanate remaining after refluxing 20 h. To the completed reaction solution was added 1551 g toluene to yield a 5 wt percent solids solution of an organic-based thermoplastic release composition containing a chemically bound uvaphor (see col. 9 of U.S. Pat. No. 2,532,011 for preparation of polyvinylcarbamates).

This solution was applied at a variety of coating weights to 50 micrometers (2 mil) polypropylene film using wire wound stainless steel coating rods (RDS coating rods, R. D. Specialties, Inc., Webster, N.Y.). RDS rod numbers 3, 4, 5, and 6, utilized for these coatings deposit wet film thicknesses of 6.9, 9.1, 11.4 and 13.7 micrometers (0.27, 0.36, 0.45, and 0.54 mils) respectively. The coated samples were dried in a forced air oven at 70° C. for 5 min and were then analyzed as in EXAMPLE 1 on a fluorescence spectrophotometer using a $\lambda_1$ of 260 nm and a $\lambda_2$ of 315 nm. Two measurements were taken for each sample and the average uvescent emission level obtained for each coating weight is reported in Table II below.

TABLE II

| Sample | Coated with RDS rod No. | Uvescent emission level |
|---|---|---|
| 5 | 3 | 27 |
| 6 | 4 | 42 |
| 7 | 5 | 50 |
| 8 | 6 | 63 |

The data of Table II show a strong correlation between coating thickness and uvescent emission level.

EXAMPLE 3

This example describes preparing a solventless epoxysiloxane release coating composition containing a chemically bound uvaphor; coating and curing the release composition on a substrate to yield release liners of varied coating weight; and analyzing the release liners on a fluorescence spectrophotometer to show the correlation between coating weight and uvescent emission level.

Into a 12-liter 3-necked round-bottom flask equipped with mechanical stirrer, pressure equalizing addition funnel, static nitrogen atmosphere, and thermometer was added 5,400 g of a trimethyl chain-stopped siloxane fluid composed of 83 mole % dimethylsiloxane units and 16 mole % methylhydrogensiloxane units having a viscosity of 200 cps, and 4 liters toluene (see U.S. Pat. No. 4,313,988 for preparation of SiH prepolymers). A solution consisting of 1250 g allylglycidylether, 800 ml toluene, and 1.13 g of a solution composed of 10 wt % chloroplatinic acid and 90 wt % isopropanol was stirred at room temperature for 16 h. before charging to the pressure equalizing addition funnel. The flask was heated to 75° C. and maintained at this temperature as the catalyzed allylglycidylether solution was added dropwise over a period of 7 h. Heating was continued for 48 h. before a second solution composed of 120 g allylglycidylether, 100 ml toluene, 60 g 9-allylfluorene and 0.375 g of the chloroplatinic acid/isopropanol solution used previously was charged to the pressure equalizing addition funnel. This second solution, containing allylglycidylether and a reactive uvescer, was added dropwise over a period of 2 h. and heating was continued for 16 h. more before the completed reaction was cooled to room temperature. The reaction solution was devolatilized by passing through a thin film evaporator heated at 90° C. and at a pressure of 0.5 torr over a period of 8 h. The resultant polymer having the approximate formula

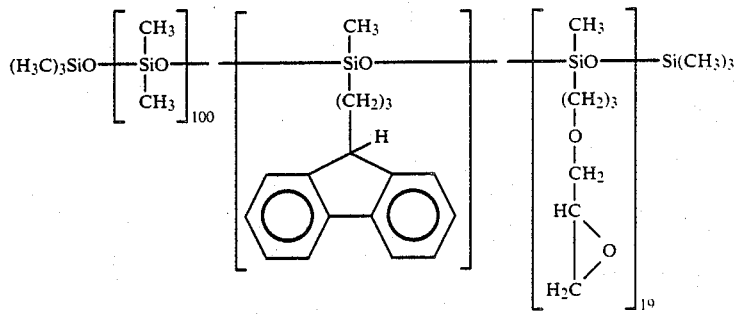

was a solventless epoxysiloxane release polymer containing a chemically-bound uvaphore, and having a viscosity of 475 cps and an epoxy equivalent weight of 612 g.

An actinic-radiation-activated catalyst was prepared by dissolving 1 part of triphenylsulfonium hexafluoroantimonate in a mixture of 25 parts of methylene chloride and 10 parts of ethanol and adding 1 part of fumed silica (Cab-O-Sil M5 ™). The mixture was stirred for 15 minutes, filtered to remove solvent and was then air-dried overnight at 25° C. After drying, the silica-supported catalyst was powdered by means of a mortar and pestle and 4 g of this powdered catalyst and 96 g of epoxysiloxane polymer were mixed together for 10 min. to obtain a solventless UV radiation curing epoxysiloxane release coating composition containing a chemically bound uvaphore.

The silicone coating composition was then applied to 90-micrometers-thick (3.5 mil) TiO$_2$-filled polypropylene film using the equipment and technique described in EXAMPLE 1. The transfer and back-up rolls turned at 30.4 m/min. (100 ft/min.) and the surface speed of the gravure roll was varied from 1.5-4.6 m/min. (5-15 ft/min.) to provide 5 samples of different coating weight. The 5 samples were then passed through a UV processing apparatus (consisting of four 30.5 cm (12 inch) medium-pressure mercury lamps, each emitting 120 watts/centimeter) at a speed of 30.5 m/min to provide samples of cured epoxysiloxane release liners. The resultant coating weights were measured using a fluorescent chemical analyzer as in EXAMPLE 1 and the average of 10 measurements from each sample showed average coating weights of the 5 samples to be 0.37 g/m², 0.33 g/m², 0.31 g/m², 0.24 g/m², and 0.10 g/m², respectively. The 5 samples of release liners were then analyzed on a fluorescence spectrophotometer as in EXAMPLE 1 using a $\lambda_1$ of 260 nm and a $\lambda_2$ of 315 nm, except that 8 measurements per sample were taken rather than the 5 measurements per sample taken previously. The average fluorescent emission level for each coating weight is recorded in Table III.

TABLE III

| Sample | Coating weight (g/m²) | Uvescent emission level |
|---|---|---|
| 9 | 0.37 | 85 |
| 10 | 0.33 | 82 |
| 11 | 0.31 | 72 |
| 12 | 0.24 | 49 |
| 13 | 0.10 | 25 |

The data of Table III show excellent correlation between coating weight and uvescent emission level.

EXAMPLE 4

This example describes a solvent based pressure-sensitive acrylic adhesive coating composition containing a soluble, essentially non-volatile uvescer; coating and drying the adhesive composition on a substrate to provide adhesive tapes of varied coating weight; and analyzing the adhesive tapes on a fluorescence spectrophotometer to show the correlation between coating weight and uvescent emission level.

To 99.97 g of a 25% solids 70:30 heptane:isopropanol solution of a pressure-sensitive adhesive comprised of 95.5:4.5 isooctyl acrylate:acrylic acid copolymer was added 0.03 g 9-allylfluorene. This solution was agitated overnight to adequately disperse the uvescer in the adhesive before coating.

This solution was applied at a variety of coating weights to 51 micrometer (2 mil) poly(ethylene terephthalate) film using a conventional knife coating apparatus. Five samples were coated using orifice settings of 76, 102, 127, 152, and 178 micrometers, respectively (3, 4, 5, 6, and 7 mils, respectively). The coated samples were dried in a forced air oven at 70° C. for 5 minutes to remove solvent and then analyzed by gravimetric analysis to obtain coating weights. The coating weights of the 5 samples were found to be 27.4, 37.3, 43.6, 53.8, and 62.4 g/sq.m respectively. These samples were then analyzed on a fluorescence spectrophotometer as in EXAMPLE 1 using an excitation wavelength of 253 nm and monitoring uvescent emission at 315 nm. Sixteen measurements were taken for each coating and the average uvescent emission level for each coating is reported in Table IV.

TABLE IV

| Sample | Coating weight (g/m²) | Uvescent emission level |
|---|---|---|
| 14 | 27.4 | 18.6 |
| 15 | 37.3 | 34 |
| 16 | 43.6 | 44 |
| 17 | 53.8 | 75 |
| 18 | 62.4 | 84.9 |

The data of Table IV show excellent correlation between coating weight and uvescent emission level.

Various modifications and alterations of this invention will become apparent to those skilled in the art without departing from the scope and spirit of this invention, and it should be understood that this invention is not to be unduly limited to the illustrative embodiments set forth herein.

I claim:

1. A process for monitoring functional coating compositions applied to a substrate comprising the steps:
    (a) providing a functional coating composition comprising an effective amount of a uvescer that absorbs radiant energy of a wavelength range centered around $\lambda_1$ and emits radiant energy of a wavelength range centered around $\lambda_2$, $\lambda_1$ and $\lambda_2$ each being a wavelength up to 400 nm within the ultraviolet portion of the electromagnetic spectrum; and the mean of the range of $\lambda_1$ being below the mean of the range of $\lambda_2$;
    (b) coating a substrate with a layer of said functional coating composition;
    (c) scanning the resulting coating with radiant energy of a wavelength range centered around $\lambda_1$; and
    (d) detecting the radiant energy of a wavelength range centered around $\lambda_2$ emitted by said coating.

2. The process according to claim 1 further comprising the step of correlating said emitted radiant energy to independently measured standard weights or thicknesses, so as to measure coating weight, thickness, uniformity, or defects of said coating.

3. The process according to claim 1 further comprising the step of curing said resulting coating by means of heat or exposure to actinic or to electron-beam radiation.

4. The process according to claim 1 wherein the functional coating composition is selected from protective coatings, adhesive coatings, priming coatings, low adhesion backsize coatings, radiation-sensitive imageable coatings, and release coatings.

5. The process of claim 4 wherein said substrate (1) fluoresces at a wavelength above 350 nanometers or (2) does not fluoresce.

6. The process of claim 1 wherein $\lambda_1$ is in the range of 240 to 400 nm and $\lambda_2$ is in the range of 280 to 400 nm.

7. The process according to claim 1 wherein $\lambda_1$ is in the range of 240 to 400 nanometers and $\lambda_2$ is a wavelength below 400 nanometers.

8. The process of claim 1 wherein said uvescer is a polycyclic aromatic compound that (a) absorbs radiant energy of a wavelength within the range of 240 to 400 nm and emits radiant energy of a wavelength below 430 nm of which less than 30% has a wavelength above 400 nm and (b) has a product ($\epsilon\phi$) of molar extinction coefficient ($\epsilon$) and quantum yield ($\phi$) of at least 1000.

9. The process of claim 8 wherein said uvescer has a product ($\epsilon\phi$) of molar extinction of 10,000 or more.

10. The process of claim 1 wherein said uvescer is selected from biphenyl, triphenylbenzene, fluorene, carbazole, terphenyl, quaterphenyl, triphenylene, naphthalene, 2,5-diphenylfuran, dibenzofuran, 2,5-diphenyl-1,2,4-oxadiazole, and their derivatives.

11. The process of claim 1 wherein said uvescer is 9-allylfluorene.

12. The process according to claim 1 wherein said detecting is of a pattern of marks, images, or codes.

13. The process according to claim 1 wherein said uvescer is chemically bound in said coating composition.

14. The process according to claim 1 wherein said uvescer is soluble in said coating composition.

15. The process according to claim 1 wherein said uvescer is dispersed in said coating composition.

16. A process for monitoring the thickness of functional coating compositions applied to a substrate comprising the steps:
  (a) providing a functional coating composition comprising an effective amount of uvescer that absorbs radiant energy of a wavelength range centered around $\lambda_1$ and emits radiant energy of a wavelength range centered around $\lambda_2$, $\lambda_1$ and $\lambda_2$ each being a wavelength up to 400 nm within the ultraviolet portion of the electromagnetic spectrum; and the mean of the range of $\lambda_1$ being below the mean of the range of $\lambda_2$;
  (b) coating a substrate with a layer of said functional coating composition;
  (c) scanning the resulting coating with radiant energy of a wavelength range centered around $\lambda_1$; and
  (d) detecting the radiant energy of a wavelength centered around range $\lambda_2$ emitted by said coating.

17. The process according to claim 16 further comprising the step of correlating said emitted radiant energy to independently measured standard weights or thicknesses so as to measure the coating weight thickness.

18. The process according to claim 16 further comprising the step of curing said resulting coating by means of heat or exposure to actinic or to electron-beam radiation.

19. The process according to claim 16 wherein the functional coating composition is selected from protective coatings, adhesive coatings, primary coatings, low adhesion backsize coatings, radiation-sensitive imageable coatings, and release coatings.

20. The process according to claim 16 wherein $\lambda_1$ is in the range of 240 to 400 nanometers and $\lambda_2$ is a wavelength below 400 nanometers.

21. The process of claim 16 wherein $\lambda_1$ is in the range of 240 to 400 nm and $\lambda_2$ is in the range of 280 to 400 nm.

22. The process of claim 16 wherein said substrate fluoresces at a wavelength above 350 nanometers.

23. The process of claim 16 wherein said substrate does not fluoresce.

24. The process of claim 16 wherein said uvescer is a polycyclic aromatic compound that (a) absorbs radiant energy of a wavelength within the range of 240 to 400 nm and emits radiant energy of a wavelength below 400 nm and (b) has a product ($\epsilon\phi$) of molar extinction coefficient ($\epsilon$) and quantum yield ($\phi$) of at least 1000.

25. The process of claim 16 wherein said uvescer has a product ($\epsilon\phi$) of molar extinction of 10.000 or more.

26. The process of claim 16 wherein said uvescer is selected from biphenyl, triphenylbenzene, fluorene, carbazole, terphenyl, quaterphenyl, triphenylene, naphthalene, 2,5-diphenylfuran, dibenzofuran, 2,5-diphenyl-1,2,4-oxadiazole, and their derivatives.

27. The process of claim 16 wherein said uvescer is 9-allylfluorene.

28. The process according to claim 16 wherein said detecting is of a pattern of marks, images, or codes.

29. The process according to claim 16 wherein said uvescer is chemically bound in said coating composition.

30. The process according to claim 16 wherein said uvescer is soluble in said coating composition.

31. The process according to claim 16 wherein said uvescer is dispersed in said coating composition.

* * * * *

UNITED STATES PATENT AND TRADEMARK OFFICE
CERTIFICATE OF CORRECTION

PATENT NO. : 4,922,113

DATED : May 1, 1990

INVENTOR(S) : Kurt C. Melancon et al.

It is certified that error appears in the above-identified patent and that said Letters Patent is hereby corrected as shown below:

Title page, item [57]:
On line 7 of the Abstract, kindly delete "$\xi_1$" and insert therefor -- $\lambda_1$ --.

Signed and Sealed this

Twenty-fourth Day of December, 1991

Attest:

HARRY F. MANBECK, JR.

Attesting Officer

Commissioner of Patents and Trademarks